(12) United States Patent
Deason et al.

(10) Patent No.: US 6,836,336 B2
(45) Date of Patent: Dec. 28, 2004

(54) INSPECTION SYSTEM CALIBRATION METHODS

(75) Inventors: Vance A. Deason, Idaho Falls, ID (US); Kenneth L. Telschow, Idaho Falls, ID (US)

(73) Assignee: Bechtel BWXT Idaho, LLC, Idaho Falls, ID (US)

( * ) Notice: Subject to any disclaimer, the term of this patent is extended or adjusted under 35 U.S.C. 154(b) by 290 days.

(21) Appl. No.: 10/267,320

(22) Filed: Oct. 8, 2002

(65) Prior Publication Data

US 2004/0066516 A1 Apr. 8, 2004

(51) Int. Cl.⁷ .................................................. G01B 9/02
(52) U.S. Cl. ........................ 356/502; 356/450; 356/432
(58) Field of Search ............................... 356/450, 432, 356/502, 503, 457, 458

(56) References Cited

U.S. PATENT DOCUMENTS

| | | | |
|---|---|---|---|
| 5,131,748 A | 7/1992 | Monchalin et al. | |
| 5,827,971 A | 10/1998 | Hale et al. | |
| 6,401,540 B1 | 6/2002 | Deason et al. | |
| 6,486,962 B1 | * 11/2002 | Telschow et al. | ........... 356/503 |

OTHER PUBLICATIONS

Telschow et al, UHF Acoustic Microscopic Imaging of Resonator Motion, Utrasonic Symposium, 2000 IEEE, 631–634, vol. 1, 2000.

Deason et al, Ultrasonic Imaging of Subsurface Objects Using Photorefractive Dynamic Holography, Proc. SPIE, vol. 4448, p. 153–158, Nov. 2001.

Telschow et al, Direct Imaging of Traveling Larrb Waves in Plates Using Photorefractive Dynamic Hologyraphy, J. Acoust. Soc. Am, 106(5):2578–2587, 1999.

Telschow et al, Imaging Laser Ultrasonic Measurement of the Elastodynamic Properties of Paper, Ultrasonics Symposium, 2001 IEEE, p. 737–745.

* cited by examiner

Primary Examiner—Andrew H. Lee
(74) Attorney, Agent, or Firm—Wells, St. John P.S.

(57) ABSTRACT

An inspection system calibration method includes producing two sideband signals of a first wavefront; interfering the two sideband signals in a photorefractive material, producing an output signal therefrom having a frequency and a magnitude; and producing a phase modulated operational signal having a frequency different from the output signal frequency, a magnitude, and a phase modulation amplitude. The method includes determining a ratio of the operational signal magnitude to the output signal magnitude, determining a ratio of a 1st order Bessel function of the operational signal phase modulation amplitude to a 0th order Bessel function of the operational signal phase modulation amplitude, and comparing the magnitude ratio to the Bessel function ratio.

31 Claims, 3 Drawing Sheets

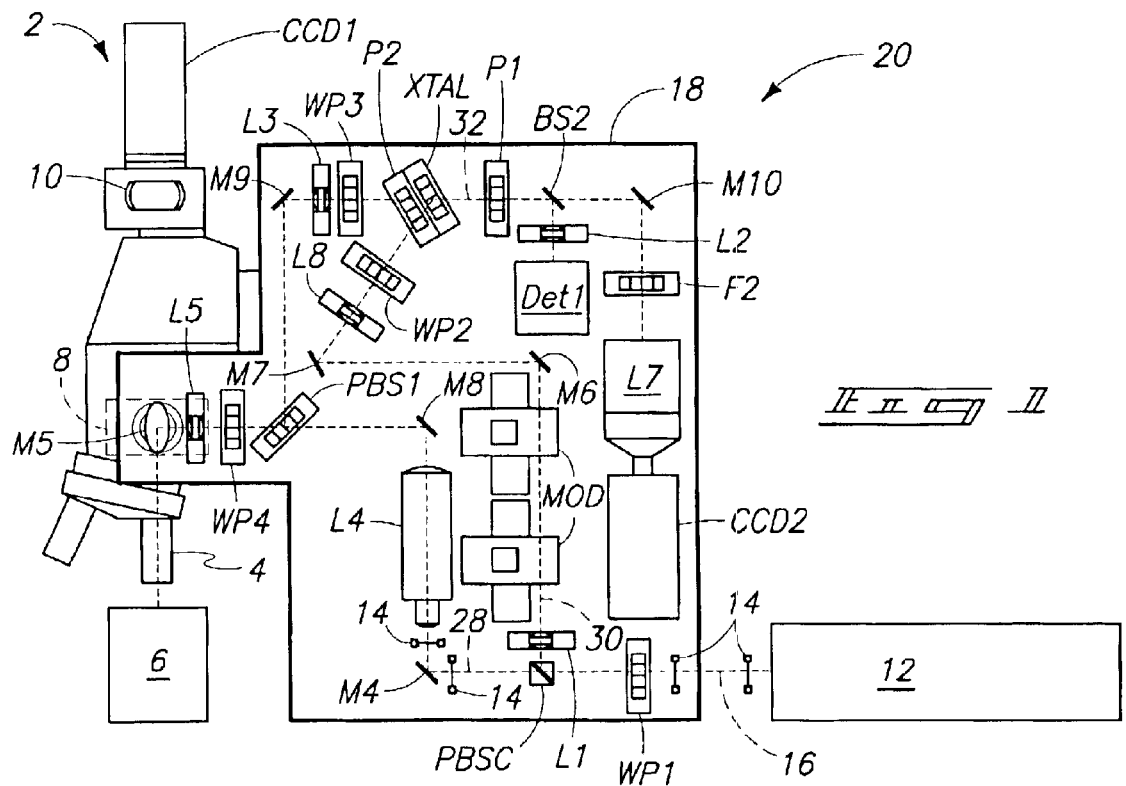
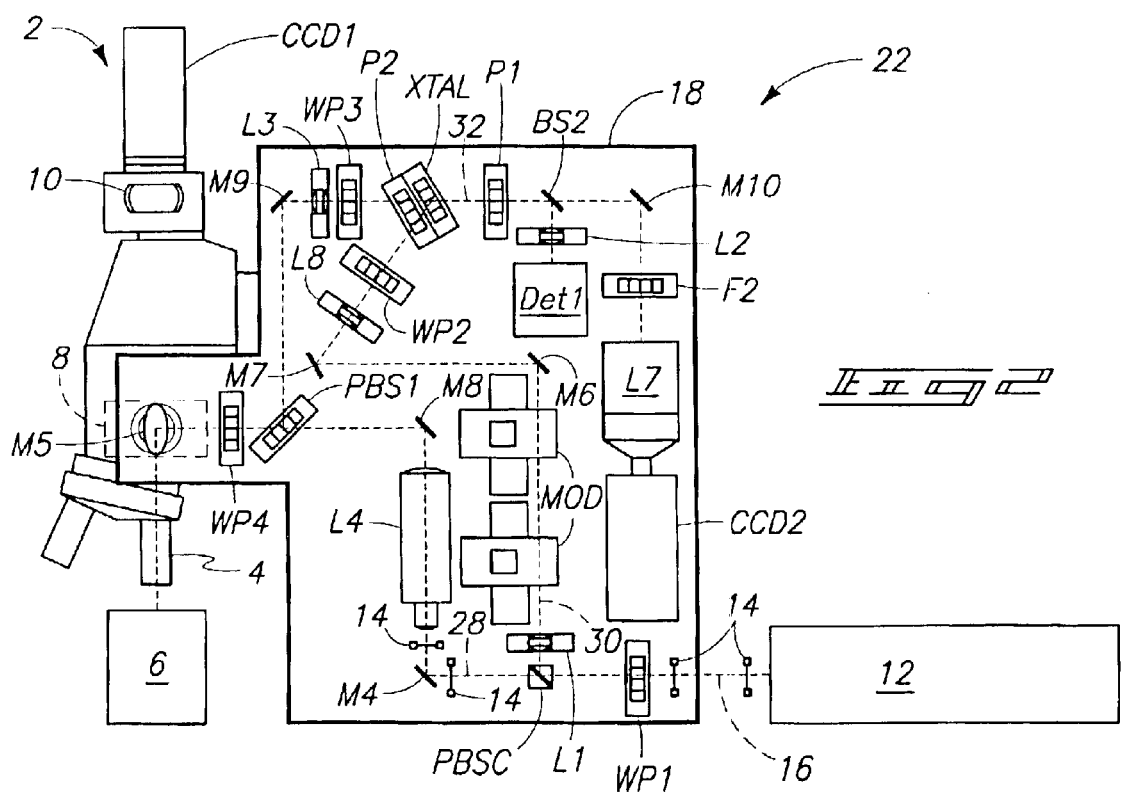

INSPECTION SYSTEM CALIBRATION METHODS

RELATED APPLICATION DATA

The present application is related to U.S. patent application Ser. No. 09/393,854, filed on Sep. 9, 1999, U.S. Pat. No. 6,175,411, filed on Jul. 8, 1998, U.S. Pat. No. 6,134,006, filed on Feb. 25, 1998, U.S. Pat. No. 6,401,540, file on Feb. 20, 2000, and to U.S. Pat. No. 5,827,971, filed on Jan. 22, 1997, each of which is incorporated herein by reference for its pertinent and supportive teachings.

GOVERNMENT RIGHTS

This invention was made with United States government support under Contract No. DE-AC07-99ID13727 between the U.S. Department of Energy and Bechtel BWXT Idaho, LLC. The United States government has certain rights in this invention.

TECHNICAL FIELD

This invention relates generally to apparatuses and methods for inspecting and/or characterizing materials, and more particularly to ultrasonic imaging of such materials in combination with optical microscopy devices. The invention also relates to inspection system calibration methods.

BACKGROUND OF THE INVENTION

The term "acoustic microscopy" traditionally referred to the use of high frequency ultrasound to probe the microstructural form and composition of an object. Traditional pulse/echo techniques were employed. Measurement of acoustic amplitude and phase were done either by contacting ultrasonic probes, or by optical interferometry through a microscope. Data for a particular point on a subject surface were obtained and useful images of the overall surface could be built up by raster scanning the object beneath the microscope.

The prevalence of micrometer scale mechanical features, microelectromechanical structures (MEMS), integrated circuits, microstructured materials, etc. is increasing. An accompanying need exists to probe the surface and subsurface physical, mechanical, and defect characteristics of such features, devices, and materials. However, conventional acoustic microscopy does not possess adequate resolution to produce reliable images and does not produce a real-time image of a surface since data is compiled over time from individual analysis points. Accordingly, the usefulness of conventional techniques are limited.

Telschow, et al., "UHF Acoustic Microscopic Imaging of Resonator Motion," 2000 *IEEE Ultrasonics Symposium Proceedings*, October 22–25, Vol. 1, 631–634 (2000), describe a beginning attempt at overcoming the deficiencies of acoustic microscopy indicated above and otherwise recognized by those of ordinary skill. Telschow, et al. acknowledge the desirability of obtaining images of ultrasonic motion over an entire surface of a subject within a single video frame. The reference also indicates success at mega-Hertz (MHz) frequencies, although not using microscopic techniques. As acoustic wavelengths get smaller (due to increasing frequency), they become capable of detecting smaller features and defects. MHz frequencies are but a beginning step in developing significantly useful imaging technology.

There exists a heretofore unrealized need to provide methods and apparatuses for accomplishing full-field, real-time imaging developed on the foundational principles of acoustic microscopy. While the advances to-date have provided improvements, they have not yet enabled one of ordinary skill to take the next leap into microscopic imaging with frequencies high enough to probe at useful resolutions.

SUMMARY OF THE INVENTION

According to one aspect of the invention, an inspection system calibration method includes: producing two sideband signals of a first wavefront; interfering the two sideband signals in a photorefractive material, producing an output signal therefrom having a frequency and a magnitude; and producing a phase modulated operational signal having a frequency different from the output signal frequency, a magnitude, and a phase modulation amplitude. The method also includes determining a ratio of the operational signal magnitude to the output signal magnitude, determining a ratio of a 1st order Bessel function of the operational signal phase modulation amplitude to a 0th order Bessel function of the operational signal phase modulation amplitude, and comparing the magnitude ratio to the Bessel function ratio.

According to another aspect of the invention, an inspection system calibration method includes: phase modulating a reference wavefront; producing two sideband signals of the phase modulated reference wavefront; interfering the two sideband signals in a photorefractive material, producing an output signal therefrom having a frequency and a magnitude; and interfering the phase modulated reference wavefront with an object wavefront in a photorefractive material and producing an operational signal therefrom having a frequency different from the output signal frequency, a magnitude, and a phase modulation amplitude. The method also includes the comparison of the magnitude ratio to the Bessel function ratio described above.

According to a further aspect of the invention, an inspection system calibration method includes: phase modulating a reference beam with a phase modulator; amplitude modulating a drive signal of the phase modulator and producing two sideband signals of the phase modulated reference beam; interfering the two sideband signals in a photorefractive material, producing an output signal therefrom having a frequency and a magnitude, the magnitude being measured as a root-mean-square voltage; passing an object beam though an objective of an optical microscope comprised by the inspection system and reflecting the object beam from a vibrating surface that phase modulates the object beam; and interfering the phase modulated reference beam with the phase modulated object beam in the photorefractive material, producing an operational signal therefrom having a frequency different from the output signal frequency, a magnitude measured as a root-mean-square voltage, and a phase modulation amplitude. The method also includes determining a ratio of the operational signal voltage to the output signal voltage, determining a ratio of a 1st order Bessel function of the operational signal phase modulation amplitude to a 0th order Bessel function of the operational signal phase modulation amplitude, and comparing the voltage ratio to the Bessel function ratio.

According to a still further aspect of the invention, an inspection method includes: providing an object wavefront that illuminates a vibrating surface of a subject and directing a modulated object wavefront returned from the vibrating surface to a photorefractive material; phase modulating a reference wavefront; producing two sideband signals of the modulated reference wavefront; interfering the modulated reference wavefront with the modulated object wavefront in the photorefractive material, and producing an inspection signal of the vibrating surface having a frequency, a magnitude, and a phase modulation amplitude; and interfering the two sideband signals in the photorefractive material, producing an output signal therefrom having a frequency different from the inspection signal frequency and a magnitude. The method also includes calibrating by determining a ratio of the inspection signal magnitude to the output signal magnitude, determining a ratio of a 1st order Bessel function of the inspection signal phase modulation amplitude to a 0th order Bessel function of the inspection signal phase modulation amplitude, and comparing the magnitude ratio to the Bessel function ratio.

BRIEF DESCRIPTION OF THE DRAWINGS

Preferred embodiments of the invention are described below with reference to the following accompanying drawings.

FIG. 1 is a schematic representation of an imaging system according to one aspect of the invention.

FIG. 2 is a schematic representation of an imaging system according to a second aspect of the invention.

DETAILED DESCRIPTION OF THE PREFERRED EMBODIMENTS

Figure 3:
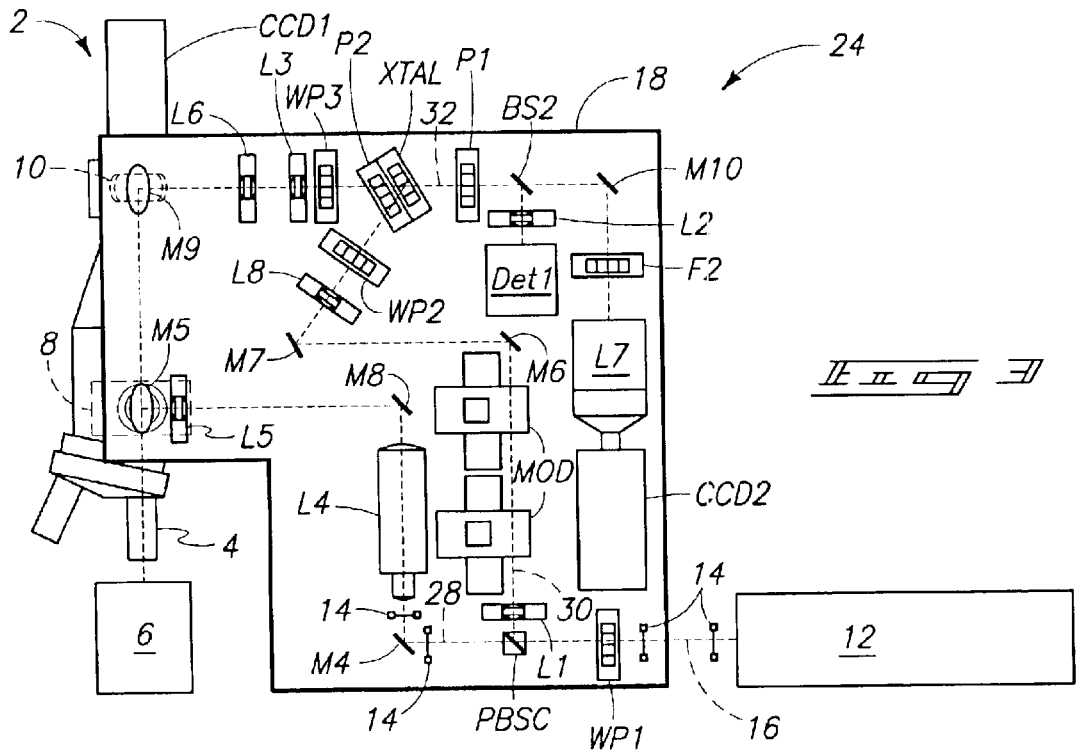
FIG. 3 is a schematic representation of an imaging system according to a third aspect of the invention.

The improvements in acoustic microscopy described herein provide various aspects of an invention useful for probing the physical, mechanical, and defect characteristics of samples at a scale of interest to industries involved in MEMS, integrated circuits, microstructured materials development, general research, etc. The patents and patent application listed in the Related Application Data section above and incorporated herein by reference provide background information regarding previous improvements in acoustic imaging that did not make use of optical microscope components. However, such background knowledge of acoustic imaging may be instructive in understanding the terminology and general concepts behind the various aspects of the present invention that combine ultrasonic imaging with optical microscopy. In particular, the background information may be instructive in understanding the various aspects of the invention that use laser ultrasonics to provide full-field, real-time imaging of acoustic resonances and waves in materials.

In the GHz range of acoustic frequencies, wave lengths are typically on the order of micrometers or less and provide a significant advancement in the resolution achievable. Specifically, a device operating at GHz frequencies is described herein. Preliminary indications exist that such technology can even be extended to higher frequencies, even approaching the terahertz range. In addition to providing full-field, real-time imaging, the various aspects of the invention may also provide a switching feature that allows small changes in the apparatus arrangement and/or method selectively to produce instead a single-point, real-time signal from a single point on a vibrating surface. Improved calibration methods are also described herein that are particularly useful with the other aspects of the invention, but may also have application to technologies not specifically described herein. One advantage of at least some aspects of the calibration method allows collection of calibrating data simultaneous with collection of inspection data. Such streamlined operation of an acoustic microscope promises improved reliability of inspection data and reduced personnel time to produce desired images.

According to one aspect of the invention, an imaging system includes an optical microscope imaging means for providing an object wavefront that illuminates a vibrating surface of a subject and for directing a modulated object wavefront returned from the vibrating surface. The optical microscope imaging means may also be used to collect the modulated object wavefront returned from the vibrating surface. The system includes a photorefractive demodulation means for interfering a reference wavefront with the modulated object wavefront in a photorefractive material and for producing a full-field, real-time image signal of the vibrating surface. As an additional advantage, the system may further include a switching means for selectively producing instead a single-point, real-time signal of the vibrating surface. Other advantages can be afforded when the imaging system further includes a vibration means for applying an acoustic frequency of at least about 1 GHz.

One possibility for a switching means includes a switching lens selectively removable from a path of the object wavefront (including the modulated object wavefront) to produce the single-point signal. In the context of the present document, producing a full-field, real-time image signal is referred to as "imaging mode," and producing a single-point, real-time signal is referred to as "point measurement mode." Producing an "inspection signal" encompasses both modes. Accordingly, an "inspection system" includes the imaging systems described herein as well as others, such as systems operating only in point measurement mode. "Single-point" and "point measurement" are known to those skilled in the art as not referring to a "point" in the mathematical sense.

It is conceivable that multiple lenses or combinations of other optical components might be used to accomplish the switching function described above, depending on a particular configuration of an imaging system. The present document expressly encompasses any of the switching means conceivable by those of ordinary skill that are suitable with an imaging system having the optical microscope imaging means and photorefractive demodulation means described herein.

As can be readily appreciated, assuming equally beneficial inspection results, a simple switching means may be preferred over a more complex switching means. Accordingly, a single switching lens providing the desired feature is preferred. Of course, proper selection of a single switching lens or other switching means may involve consideration of compatibility with other optical components, in particular the optical microscope imaging means, as can be readily appreciated from the more detailed description below.

Various vibration means are also conceivable for applying a desired acoustic frequency. The vibration means may be a stand alone device, integrated with other components of the imaging system, or even be comprised by an imaging subject itself. For example, in the case where the imaging system includes a subject stage, such as an optical microscope stage, a vibration means might be integral to the subject stage. One example of a vibration means comprised by a subject itself includes ultra-high frequency (UHF) ultrasonic resonators being developed for specialized signal processing in the telecommunications industry. Operation in the 1–2 GHz frequency range is now possible and higher frequencies are contemplated. Specific examples include surface acoustic wave (SAW) and bulk acoustic wave resonator (BAR) devices. Operation at GHz frequencies has been achieved for the various aspects of the invention described herein.

The optical microscope imaging means mentioned above can include a complete optical microscope. An optical microscope typically includes a convenient set of optical components along with a microscope objective that can be useful in obtaining magnified images of a subject surface. The same applies to obtaining images of acoustic resonances and waves in a subject surface. Since an optical microscope is a compilation of various optical components, the optical microscope imaging means may be construed to include any compilation of optical components that provides the desired magnified acoustic image, whether known to those skilled in the art or later developed. Preferably, the optical microscope imaging means includes at least an microscope objective. More preferably, the optical microscope imaging means includes a complete optical microscope. The microscope may include a means for introducing and extracting the object wavefront.

A variety of optical microscopes are available that may be of use in providing an object wavefront that illuminates a vibrating surface of a subject and for directing a modulated object wavefront returned from the vibrating surface. For example, the microscope may include a laser port through which the object wavefront enters the microscope and through which the modulated object wavefront exits the microscope. Alternatively, the optical microscope can include the laser port through which the object wavefront enters the microscope, but additionally include another port through which the modulated object wavefront exits the microscope.

An illuminator port is a common component of conventional microscopes used to introduce a light source for general viewing of a subject in what is known as "epi-illumination mode." The illuminator port illuminates the subject through the microscope objective. Accordingly, the illuminator port can be configured as an exit port for the modulated object wavefront. When using an illuminator port, it is conceivable that correction for microscope optical components effects may be desirable. Thus, the optical microscope imaging means can further include a compensation lens separate from an optical microscope that compensates for the optical effects. The modulated object wavefront may pass through the compensation lens after exiting the microscope and before interfering with the reference wavefront in the photorefractive material. As but one example, the compensation lens might adjust for the increased distance from the microscope objective to the photorefractive material where the subject is "viewed" as compared to the microscope design distance from the objective to an eyepiece where the subject would normally be viewed.

Since the optical microscope imaging means both provides an object wavefront that illuminates a vibrating surface of a subject and directs a modulated object wavefront returned from the vibrating surface, the microscope imaging means can include still further components. For example, the imaging means may include a wavefront expander means for expanding the object wavefront before illuminating the vibrating surface. In one aspect of the invention, the wavefront expander means includes a wavefront expander wherein the imaging system components can be positioned to direct the object wavefront through the wavefront expander and to direct an expanded object wavefront from the wavefront expander onto the subject surface. The wavefront expander may be used to expand the object wavefront to substantially match an entrance aperture of an optical microscope. In this manner, an area of the subject surface encompassed by a field of view of the optical microscope can be illuminated by the object wavefront to the maximum extent possible. Understandably, it may be desirable merely to substantially match the entrance aperture rather than to perfectly match the entrance aperture. Also, the object wavefront may be expanded to significantly less than the entrance aperture in a circumstance where less than the full field of view of the microscope objective is to be illuminated.

The photorefractive demodulation means can similarly include a variety of components used to interfere a reference wavefront with the modulated object wavefront in a photorefractive material and to produce a full-field, real-time image signal of the vibrating surface. As one example, the photorefractive demodulation means can include an imaging lens through which the modulated object wavefront passes before reaching the photorefractive material. Such imaging lens is different from the compensation lens described above as part of the optical microscope imaging means. The imaging lens collects the wavefront from the optical microscope imaging means and forms an image in the photorefractive material.

The photorefractive demodulation means can include first and second one-half waveplates through which the reference and modulated object wavefront pass, respectively, before interfering. A number of waveplates known to those skilled in the art or later developed may be suitable. The intention is to rotate the polarization of the reference and modulated object wavefronts into adequate alignment with the photorefractive material when a photorefractive material requires such alignment. A photorefractive material such as bismuth silicon oxide (BSO) crystal may function better when the polarization of reference and object wavefronts are in a preferred alignment with the crystal. Deviation from the ideal condition of similar polarization alignment can result in a progressively greater amount of light not participating in constructive and destructive interference. Instead the light may be present as background that decreases the signal to noise ratio. Complex interaction with the crystal axis orientation can cause misaligned polarizations to create multiple interference patterns (diffraction gratings) that steal power from the desired data. Such phenomenon can be understood from the vector description of electromagnetic waves, where the electric vectors of the two interfering waves decompose into orthogonal components that either add or subtract to produce a total intensity for each component at each point in the wave.

Similarly, the photorefractive demodulation means can include a linear polarizer through which both the reference and modulated object wavefronts pass before interfering. The linear polarizer assists in improving the polarization of the wavefronts. The liner polarizer can be associated with the photorefractive material such that the reference and modulated object wavefronts both pass through the linear polarizer immediately before entering the photorefractive material. Polarization impurity can be described as mixtures of various polarizations at different angles. As just described, mismatched polarizations cause parasitic gratings that steal power from the data beam, and/or introduce a general background signal that reduces signal to noise ratio. The exact effect depends on the degree of misalignment of the polarizations of the two beams, as well as the misalignment with the critical crystal optical axes of the photorefractive material.

The photorefractive demodulation means may additionally include at least one phase modulator wherein the reference wavefront is directed through the phase modulator and modulated prior to entering the photorefractive material. The patents incorporated herein by reference describe the knowledge disclosed to those of ordinary skill regarding how to modulate the reference wavefront. The modulation occurs at an offset frequency similar to, but slightly different from, a frequency at which the object beam was modulated by the vibrating subject surface. A variety of the modulation schemes described in the incorporated patents may be suitable for the various aspects of the invention and easily adapted thereto by those of ordinary skill.

Providing more than one phase modulator can allow coverage of different bandwidths. Since the modulation effects of each may be independent, one modulator might have a broad bandwidth for scanning over a large frequency range, while the other might have a narrow bandwidth for looking at a single resonant feature within that bandwidth. Alternatively, the modulators might be tuned to widely different frequencies (for example, one at 1 GHz and another at 2 GHz) to facilitate the inspection of different types of subjects with different frequency characteristics.

Building on the concepts of phase modulation at an offset frequency and photorefractive demodulation, aspects of the present invention provide methods and apparatuses for linking advancements in the earlier technologies with an optical microscope and for increasing the acoustic frequencies used to the GHz range and potentially higher.

The imaging system can further include an image signal acquisition subsystem. The image may be recorded by any conventional recording method adaptable to the full-field, real-time image signal produced from the photorefractive material. Exemplary methods include analog or digital video, tape storage, computer memory storage, etc. Preferably, the recording method provides for further processing, as desired for some applications. One example includes a charge-coupled device (CCD) camera that may acquire the full-field image signals.

The image signal acquisition subsystem may additionally include a detector of the type conventionally used to acquire single-point signals. Including both of the signal acquisition devices is redundant in conventional acoustic microscopy, but is well suited to aspects of the invention that include the switching means described herein.

The image signal acquisition subsystem can include a linear polarizer and an intensity adjusting filter through which the image passes before being acquired. In particular, a high extinction linear polarizer is useful in improving polarization purity of the image signal and/or the single-point signal. The enhanced polarization purity provides some improvement in signal to noise ratio. Preferably, the extinction ratio is greater than about 1000:1. The intensity adjusting filter is useful to reduce the image signal input to an intensity most readily sensed by a signal acquisition device. An intensity adjusting filter is particularly beneficial for a CCD camera. One example of a suitable filter includes a polarizer that may be rotated to progressively block a portion of the image signal depending on the signal strength.

According to another aspect of the invention, an imaging system includes an object wavefront source and an optical microscope objective all positioned to direct an object wavefront onto an area of a vibrating subject surface encompassed by a field of view of the microscope objective and to direct a modulated object wavefront reflected from the encompassed surface area through a photorefractive material. A reference wavefront source and at least one phase modulator are all positioned to direct a reference wavefront through the phase modulator and to direct a modulated reference wavefront from the phase modulator through the photorefractive material to interfere with the modulated object wavefront.

The photorefractive material has a composition and an orientation such that interference of the modulated object wavefront and modulated reference wavefront occur within the photorefractive material, providing a full-field, real-time image signal of the encompassed surface area. As one example, the object wavefront source and the reference wavefront source can together include one initial wavefront emitter, a third one-half waveplate, and a polarizing wavefront splitter. Such devices are all positioned to direct an initial wavefront through the one-half waveplate and to direct a rotated initial wavefront from the one-half waveplate through the polarizing wavefront splitter. The splitter provides the object and reference wavefronts and controls the relative intensity of the object and reference wavefronts. The object and reference wavefronts may have about the same intensity to encourage optimum interference. Such phenomenon can be understood from the vector description of electromagnetic waves introduced above.

According to a further aspect, the invention combines two technologies, optical microscopy and a laser ultrasonic camera to provide real-time imaging of UHF acoustic resonances and waves in materials. A laser beam is divided into reference and object beams and the object beam is sent through the microscope where it illuminates a small region of a surface. Reflected light from the object carries phase information related to the vibrational displacements at the surface (caused by UHF acoustic waves). The reflected light is collected by the microscope and returned for optical processing by the ultrasonic camera system. There, the reference beam, after being phase modulated at a frequency similar to but slightly different from the UHF frequency, is expanded and illuminates a photorefractive material. The object beam reflected from the subject is simultaneously focused into the photorefractive material by an imaging lens so as to overlap the reference beam and hence interfere within the material.

The interference causes the well known photorefractive effect, where a diffraction grating (hologram) is formed due to electric fields caused by photo generated electrons. The grating can then diffract light that passes through it including the beams that formed the grating. As fully described in earlier patents incorporated herein by reference, the result is that the phase data contained in the object beam is demodulated and produces an image with an intensity that is locally proportional to the amplitude of the UHF vibration on the original subject. This results in an image of the distribution of acoustic waves that is fully quantitative and provides both amplitude and phase information on these waves, as well as their relationship to physical and geometric features on the subject. Most types of analysis normally performed by point measurement ultrasonic inspection can be performed by this method, but in real-time imaging mode.

The imaging system may include peripheral components, such as a sample positioning subsystem, data acquisition subsystem, conventional imaging subsystem for alignment purposes, etc. The exact configuration depends on the particular application and the requirements thereof. One aspect of the invention includes operation either in an imaging mode or a more sensitive point measurement mode. Thus, the system may include a photodetector in addition to a camera for acquiring data and may include other electronic components such as preamplifiers and lock-in amplifiers.

The point measurement mode uses illumination of the subject with a focused spot of light (rather than being uniformly illuminated as in the imaging mode). Accordingly, the sample positioning subsystem may include a mechanism for scanning the subject so as to collect data at many points on the subject surface. Alternatively, a means may be provided for scanning the laser spot on the surface.

As indicated, microscope configurations that permit illumination of a subject through the objective are advantageous, although not required. A commercial Leitz DMRME or equivalent microscope is one example that allows illumination through the objective. Alternatively, microscope subcomponents may be assembled so as to optimize a custom microscope for this particular application. It may be possible to illuminate from below, if the subject is transparent, or from the side, if the subject or microscope geometry does not prevent it.

Turning to FIGS. 1–4, imaging systems 20, 22, 24, 26 are depicted in schematics intended to represent the co-relation of the more significant components of the exemplary systems. The layouts depicted are adapted to the particular configuration of optical microscope 2 comprising part of the systems. Alterations in the particular layouts depicted are readily recognizable as within the scope of the various aspects of the invention in order to adapt the systems to other microscope configurations. In addition, even a system including identical optical components can nevertheless be laid out in a manner more or less advantageous than the systems shown in FIGS. 1–4. A variety of factors, including the particular optical and mechanical construction of the microscope, cameras, modulators, and other components used, as well as the space constraints imposed by a particular application, may influence a layout selected.

The imaging systems 20, 22, 24, 26 of FIGS. 1–4 include the bulk of the components discussed herein as advantageous in such systems. However, such components may be individually advantageous in the absence of other components shown as part of the systems in FIGS. 1–4. Various systems within the scope of the aspects of the invention might not include every component shown. Nevertheless, observation indicates that the components shown work in combination to provide a synergistic effect and a preferred linking mechanism to an optical microscope yielding highly advantageous resolution at GHz frequencies.

FIG. 1 shows imaging system 20 including optical microscope 2 with an objective 4 and a subject stage 6. Microscope 2 also includes a laser port 8 and an illuminator port 10. Laser 12 generates a beam 16 that becomes an object beam 28 and a reference beam 30, the beams passing through and being processed by the various components of imaging system 20 mounted on an optics board 18. Laser 12 is advantageously of sufficient power, beam quality, coherence, and phase stability to perform the desired measurement functions. A Coherent (TM) 2 Watt Verdi (TM) diode pumped doubled solid state laser available from Coherent Laser Group in Santa Clara, Calif. is one example.

In reality, the beam paths may be obscured when passing through some components, however, the paths are shown revealed throughout the system for clarity. The beam paths are shown generally and may differ in practice within some components, in particular, within microscope 2 for which internal details are not provided. Alignment iris 14 are provided and may be adjustable to aid in restoring beam alignment. Alignment iris 14 may be placed at a variety of locations along the beam paths to provide such function. A CCD imaging camera CCD1 is also provided to inspect microscope 2 function and align object beam 28.

A one-half waveplate WP1 is used to rotate the polarization of the incident beam 16. In combination, a polarizing beam splitting cube PBSC and one-half waveplate WP1 adjust the relative intensity of object and reference beams. Polarizing beam splitting cube PBSC splits the incident beam 16 into object beam 28 and reference beam 30. Object beam 28 is reflected from a mirror M4 into a lens L4. The various mirrors described in FIG. 1 are used to redirect beams at pertinent points. The mirrors preferably exhibit a λ/10 or better surface flatness to preserve beam quality and have high reflectivity to preserve beam power.

Lens L4 is used to expand object beam 28 before entering laser port 8 of microscope 2. Preferably, object beam 28 substantially matches the entrance aperture of microscope 2 after expansion in lens L4. A mirror M8 directs object beam 28 through a polarizing beam splitter PBS1, through a one-quarter waveplate WP4, and through a lens L5 to a mirror M5 before entering laser port 8. One-quarter waveplate WP4 is used to adjust the polarization of object beam 28 such that it may be both introduced and extracted from laser port 8. Lens L5 is used to adjust object beam 28 to substantially match the numerical aperture (NA) of microscope 2 to insure uniform illumination of a subject on subject stage 6. The adjusted object beam 28 from lens L5 is reflected from mirror M5 through an opening (not shown) in optics board 18 toward laser port 8.

After object beam 28 enters microscope 2, it encounters a beam splitter that directs the beam downward to pass through objective 4 and illuminate a subject on subject stage 6, reflecting therefrom as a modulated beam. Object beam 28 so modulated exits laser port 8, reflects from mirror M5 and passes through lens L5 and one-quarter waveplate WP4, thus converting object beam 28 polarization from circular to linear so as to align the polarization angle with PBS1. Polarizing beam splitter PBS1 separates the portion of object beam 28 returning modulated and the portion of object beam 28 traveling toward microscope 2. Object beam 28 then reflects from a mirror M9 and passes through a lens L3, a one-half waveplate WP3, and a linear polarizer P2 before entering a photorefractive crystal XTAL. The imaging lens collects light from the optical microscope imaging means and creates an image of ultrasonic data in the photorefractive material. One-half waveplate WP3 rotates the polarization of object beam 28 into preferred alignment with photorefractive crystal XTAL and reference beam 30. Linear polarizer P2 is used to improve the polarization of object beam 28 prior to interfering inside photorefractive crystal XTAL with reference beam 30.

In tandem with object beam 28 modulation at microscope 2, reference beam 30 undergoes phase modulation. Reference beam 30 passes through a lens L1 used to adjust beam diameter to fit modulators MOD. While FIG. 1 shows two modulators MOD, it is to be understood that the invention encompasses one or more modulators. The modulators are preferably electro-optic modulators.

After phase modulation, reference beam 30 reflects from a mirror M6 and mirror M7 toward a one-half waveplate WP2. Depending on particular circumstances, a second imaging lens L8 may be useful between mirror M7 and one-half waveplate WP2 to recollimate reference beam 30 at an optimum diameter for illuminating photorefractive crystal XTAL. One-half waveplate WP2 rotates the polarization of reference beam 30 into preferred alignment with photorefractive crystal XTAL and object beam 28. Linear polarizer P2 processes reference beam 30 in a similar manner to object beam 28, improving the polarization of reference beam 30 before interfering inside photorefractive crystal XTAL. Although not shown, independent linear polarizers for each of the object and reference beams may instead be used. The photorefractive effect occurring within photorefractive crystal XTAL produces an operational signal 32.

For imaging system 20, operational signal 32 comprises a full-field, real-time image signal of the microscope 2 subject and passes through a linear polarizer P1 used to improve the polarization purity of operational signal 32 before entering a detector DET1 or a CCD digital camera CCD2. Linear polarizer P1 assists in improving signal to noise ratio and may exhibit a high extinction ratio of greater than 1000:1. A beam splitter BS2 divides operational signal 32 and a portion of operational signal 32 reflects from a mirror M10 through a filter F2 used to adjust the intensity of the signal received by CCD digital camera CCD2. Although not shown, a similar filter may be advantageous in association with CCD imaging camera CCD1. Filter F2 can be a polarizer rotatable in a manner to progressively block light.

Operational signal 32 then passes through a lens L7 creating an image of ultrasonic data on CCD digital camera CCD2. Since operational signal 32 comprises a full-field, real-time image signal, the use of detector DET1 and a lens L2 is not discussed in association with FIG. 1. Such devices are advantageously comprised by imaging system 20, but would generally not be utilized in the absence of modification to produce operational signal 32 as a single-point, real-time signal.

FIG. 2 shows imaging system 22 that is identical to imaging system 20 of FIG. 1, except for the removal of lens L5. Removal of lens L5 switches the imaging system to point measurement mode. Accordingly, operational signal 32 passing through lens L2 is collected and focused into detector DET1 which acquires the ultrasonic data in point measurement mode.

Figure 4:
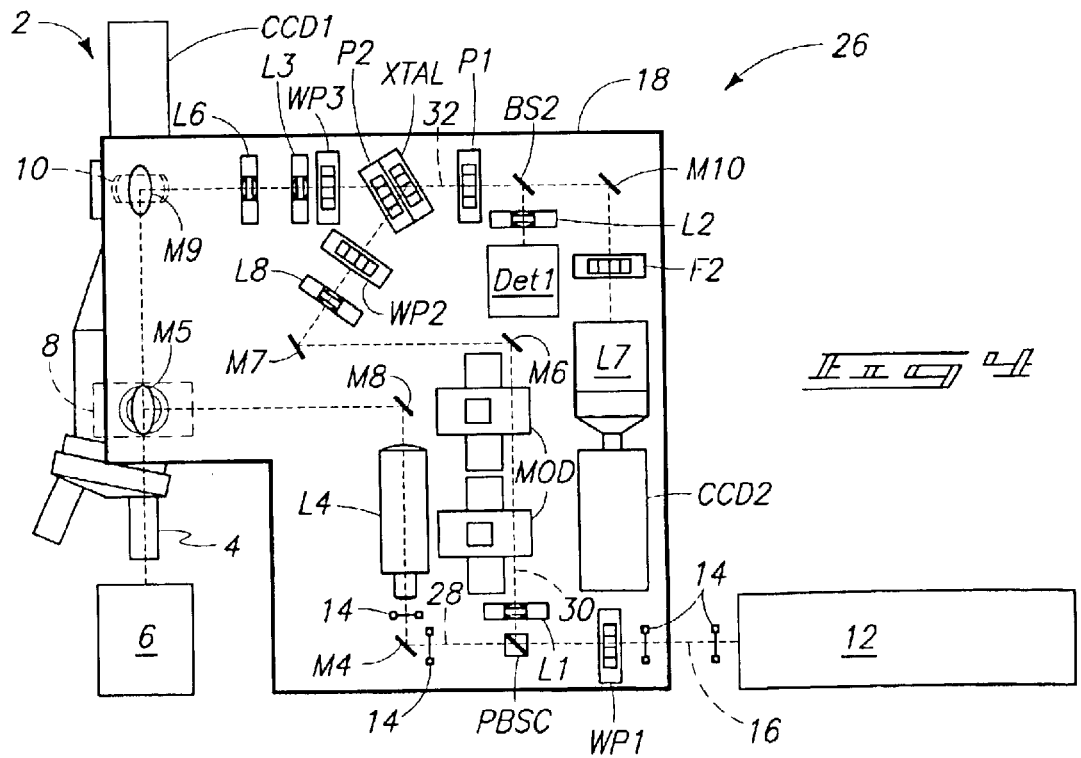
FIG. 4 is a schematic representation of an imaging system according to a fourth aspect of the invention.

FIG. 3 shows an imaging system 24 similar to that described above for FIG. 1 except that a different port is used for object beam 28 exiting microscope 2. Specifically, after being modulated, object beam 28 passes upward through microscope 2 to illuminator port 10 where it exits microscope 2. Given the change in configuration, imaging system 24 does not include polarizing beam splitter PBS1 or one-quarter waveplate WP4. Mirror M9 is relocated to illuminator port 10 to reflect object beam 28 exiting therefrom. Notably, a lens L6 is added through which object beam 28 passes after exiting illuminator port 10 and before passing through lens L3. Lens L6 may be useful to compensate for microscope optical component effects resulting from use of illuminator port 10. Accordingly, operational signal 32 comprises a full-field, real-time image signal similar to that provided in the imaging system according to FIG. 1. Imaging system 26 of FIG. 4 is identical to imaging system 24 of FIG. 3 except for the removal of lens L5. Accordingly, operational signal 32 in imaging system 26 comprises a single-point, real-time signal.

Various methods of imaging are readily apparent from the descriptions herein of selected aspects of an imaging system. In addition to the imaging methods inherently described and integral with such discussion, another aspect of the invention includes combining calibrating with producing an inspection signal, that is, a signal that may be either an image signal or a single-point signal. Such an inspection method includes providing an object wavefront that illuminates a vibrating surface of a subject, directing a modulated object wavefront returned from the vibrating surface to a photorefractive material, and phase modulating a reference wavefront. The method includes producing two sideband signals of the modulated reference wavefront and interfering the two sideband signals in a photorefractive material. The modulated reference wavefront and modulated object wavefront are also interfered in the photorefractive material, producing an inspection signal of the vibrating surface having a frequency, a magnitude, and a phase modulation amplitude. The interfered sideband signals produce an output signal having a frequency different from the inspection signal frequency and a magnitude.

The method further includes determining a ratio of the inspection signal magnitude to the output signal magnitude and determining a ratio of a 1st order Bessel function of the inspection signal phase modulation amplitude to a 0th order Bessel function of the inspection signal phase modulation amplitude. Calibrating may occur by comparing the magnitude ratio to the Bessel function ratio. The inspection method is particularly applicable to the devices described herein that include an optical microscope objective. Accordingly, the method may include passing the object wavefront through the objective and returning the modulated object wavefront through the objective prior to interfering with the phase modulated reference wavefront.

As an example, the inspection method can further include acquiring the inspection signal, wherein the acquiring occurs simultaneously with determining the magnitude ratio. Preferably, the inspection signal is a single-point, real-time signal. Calibrating in the point measurement mode simplifies operation of the method and interpretation of results. However, the inspection method is expected to be equally applicable to imaging mode. One way in which the method might be quantitatively applied to imaging mode is to calibrate each pixel of a CCD camera or a group of pixels corresponding to the diameter of the single-point. Pixel calibration methods known to those skilled in the art may be combined with the calibration methods herein.

In a related approach, both CCD imaging camera CCD1 and detector DET1 may participate in imaging mode calibration. Normally, the point measurement mode takes light from a single illuminated point (all other points being dark) on the specimen and focuses it into detector DET1. However, in the imaging mode, where the whole field of view of the specimen is illuminated, focusing the single illuminated point into detector DET1 may be simulated. An image signal blocking structure, such as a mask, may be used to block most of the image signal, while allowing only part to pass through and to simulate the signal of point measurement mode from one point location on the specimen. As an example, a mask with a single hole may be placed in imaging system 20 of FIG. 1 between beam splitter BS2 and detector DET1. Calibration on the resulting simulated point may be correlated with the image signal for the pixel or group of pixels that correspond to the point on the specimen. The correlated pixel(s) may thus be used to calibrate the entire CCD array using a separate (earlier) calibration process that provides relative responses for each pixel or group of pixels of the array. Alternatively, for at least some vibrational modes that affect most or all of the viewed area of the specimen at once (like a "piston" vibrational mode), one can collect most or all of the light from the encompassed surface area and focus it into DET1 as a single point.

Even though calibration methods are described herein that are particularly useful with other aspects of the invention, such calibration methods may also have application to technologies not specifically described herein. According to one aspect of the invention, an inspection system calibration method includes producing two sideband signal from a first wavefront, interfering the two sideband signals in a photorefractive material, and producing an output signal therefrom having a frequency and a magnitude. The method includes producing a phase modulated operational signal having a frequency different from the output signal frequency, a magnitude, and a phase modulation amplitude. A ratio of the operational signal magnitude to the output signal magnitude may be determined along with a ratio of a 1st order Bessel function of the operational signal phase modulation amplitude to a 0th order Bessel function of the operational signal phase modulation amplitude. The magnitude may be compared to the Bessel function ratio.

As will readily appreciated, producing the phase modulated operational signal can include phase modulating the first wavefront and interfering the phase modulated first wavefront with an object wavefront in a photorefractive material. Notably, the object wavefront need not be phase modulated for the calibration method. However, it may be if desired. In the context of calibrating for acoustic microscopy, this means that the calibration method may be performed both when a subject surface is vibrating as well as when it is not vibrating. Since the calibration method may be performed while phase modulating the object wavefront, it is an advantage of the calibration method to perform calibration while producing an inspection signal. Accordingly, the first wavefront may include a reference wavefront and the object wavefront may include a modulated object wavefront reflected from a vibrating subject surface. Preferably, the operational signal thus includes a single-point, real-time signal of the subject surface.

Producing the two sideband signals used in the calibration method may include phase modulating the first wavefront with a phase modulator using an amplitude modulated drive signal. The first wavefront may be a reference wavefront used in acoustic microscopy. Accordingly, the amplitude modulated drive signal may be applied to an electro-optic modulator. Also, instead of producing an operational signal using photorefractive demodulation, the phase modulated operational signal may be produced by phase modulating the first wavefront. In the context of acoustic microscopy, the reference wavefront may thus be phase modulated to produce the operational signal used in the calibration method.

Telschow, et al., "UHF Acoustic Microscopic Imaging of Resonator Motion," 2000 *IEEE Ultrasonics Symposium Proceedings*, October 22–25, Vol. 1, 631–634 (2000), describe a calibration method used to mathematically calculate and experimentally verify a phase modulation amplitude for which an operational signal is maximized. Generating the maximum operational signal assists in detecting and processing such signal and may be of use with some aspects of the invention.

The out-of-plane motion of a vibrating surface produces a phase shift of an optical beam reflected normal to the surface as determined by $$\varphi_S(t) = \frac{4\pi\xi}{\lambda} \qquad \text{(Equation 1)}$$

where $\phi_S(t)$ represents phase shift as a function of time (t), $\lambda$ is the optical wavelength, and $\xi$ is the surface displacement as determined by $$\xi(t) = \xi_0 \cos(2\pi f t + \psi) \qquad \text{(Equation 2)}$$

where f is the frequency and $\psi$ is the acoustic phase. Combining this beam with a reference beam phase modulated in a similar manner at the offset frequency of $f \pm \Delta f$, produces an interference pattern with a narrowband component varying at the frequency $\Delta f$. Two-wave mixing within the photorefractive material produces an output beam with intensity of the narrowband component of:

$$|I_{AC}| \propto J_0(\phi_S) J_1(\phi_S) J_0(\phi_R) J_1(\phi_R) \qquad \text{(Equation 3)}$$

where $|I_{AC}|$ is the intensity, $\phi_S, \phi_R$ are the optical phase modulation depths (amplitudes) on the signal (i.e., object) and reference beams, respectively, and $J_0, J_1$ are $0^{th}$ and $1^{st}$ order Bessel functions, respectively.

Figure 5:
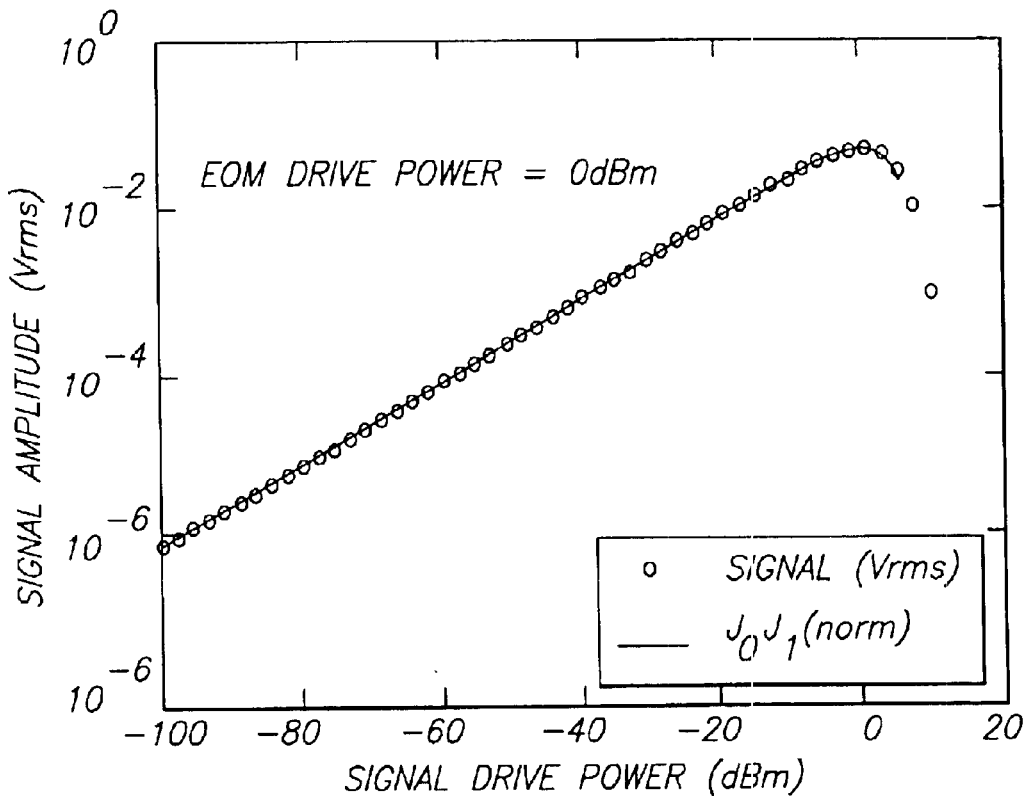
FIG. 5 represents calibration data used to determine maximum signal amplitude for varying amplitude modulation depth by increasing signal drive power of an electro-optic modulator.

It is apparent that both the object and reference beam modulations produce an output intensity proportional to the product of the $0^{th}$ and $1^{st}$ order Bessel functions. This particular Bessel function product has a maximum value for a modulation depth of $\delta = 1.08$ radians and is proportional to $\delta$ for smaller modulations. At an optical wavelength of 532 nm, this maximum value corresponds to an ultrasonic displacement of 45.8 nm. FIG. 5 shows the results of measuring this response by driving an electro-optic modulator (EOM) as a function of amplitude at fixed frequency. Maximum phase modulation depth occurs at an input drive power to an amplifier/splitter chain of about 0 dBm for the amplifier and modulator used. This resulted in a power of about 1 Watt delivered to the EOM, which was matched to 50 Ohms at 880 MHz. The solid line in the FIG. 5 shows the expected Bessel function product.

The achievement of the maximum phase modulation provided a simple means of calibration with three phase locked signal generators, two UHF generators (one each for the object and EOM modulations), and a low frequency generator to produce the difference frequency. For calibration, the two signals were combined on the EOM and the resultant signal phase shift was recorded with fixed drive power on the EOM. The result agreed very well with Equation 3 as shown in the FIG. 5.

The phase modulation amplitude that produces a maximum operational signal as determined by Telschow, et al. can be useful in an inspection system calibration method. According to one aspect of the invention, the EOM drive signal is amplitude modulated (AM) at a frequency easily separated from the operational frequency of the measurement. The result of the AM is to create two sideband signals on the phase modulated light beam. These two sideband signals also mix in the photorefractive phase detection scheme, as any phase modulation would, creating an output intensity signal at the AM frequency. The amplitudes of these sidebands are well known and can be easily measured simultaneously to the operational measurement with an additional lock-in amplifier tuned to the AM frequency. Some reduction in amplitude of the operational frequency signal occurs, but this amount is well characterized and has been confirmed in the laboratory.

Figure 6:
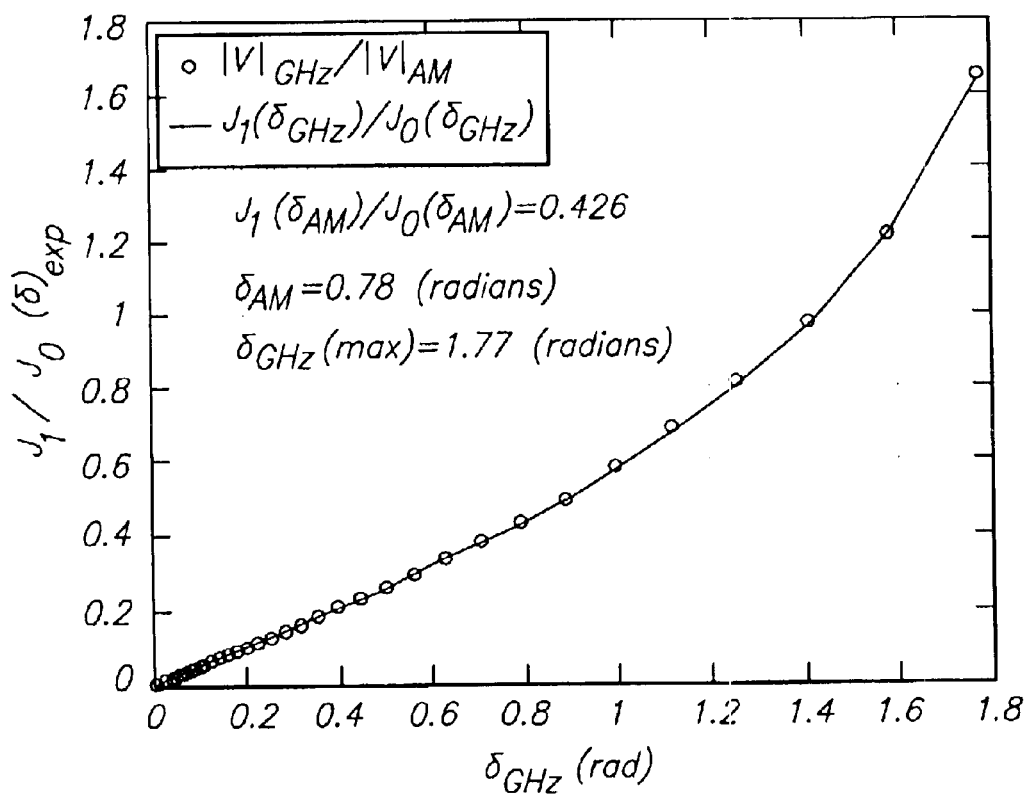
FIG. 6 represents calibration data used to verify concurrence of a signal amplitude ratio with mathematically predicted values.

Since both the AM and the operational phase signals are detected simultaneously using exactly the same optical and electrical parameters, an exact calibration is possible by simply calculating the ratio of these two signals. Analysis of the process has shown that the ratio of the two signals produces an output as follows:

$$\frac{|V_{GHz}(\text{rms})|}{|V_{AM}(\text{rms})|} = \left(\frac{J_1(\delta_{EOM})}{J_0(\delta_{EOM})}\right)\left(\frac{J_1(\delta_{GHz})}{J_0(\delta_{GHz})}\right)\left(\frac{J_0(\delta_{AM})}{J_1(\delta_{AM})}\right)$$ (Equation 4)

where $J_1, J_0(\delta)$ are Bessel functions of the phase amplitude in radians of order 1 and 0, respectively, $V_{GHz}$ (rms) is the operational signal magnitude (root-mean-square), $V_{AM}$ (rms) is the AM signal magnitude (root-mean-square), $\delta_{EOM}$ is the phase modulation amplitude in radians on the EOM, $\delta_{GHz}$ is the phase modulation amplitude being measured as the operational signal, and $\delta_{AM}$ is the phase modulation amplitude of the AM produced on the reference beam through the EOM. The $\delta_{EOM}$ selected for the instrumentation controls was 1.08 radians as determined by Telschow, et al. The $\delta_{AM}$ selected for the instrumentation controls was 0.78 radians. FIG. 6 shows a good agreement of this analysis with actual measurement.

An absolute measure of the operational signal is obtained by solving Equation 4 in reverse for the operational signal phase modulation amplitude and then calculating the acoustic displacement corresponding to the operational signal through $$\xi(\text{nm}) = \delta(\text{radians})\left(\frac{\lambda(\text{nm})}{4\pi}\right)$$ (Equation 5)

In the method described above, operational signal magnitude and AM signal magnitude were measured as voltages using a detector such as detector DET1 shown in FIGS. 2 and 4 for acquiring ultrasonic data in point measurement mode. Accordingly, the magnitude ratio constituted a voltage ratio. Even though it is preferred to calculate the magnitude ratio using root-mean-square voltages, those of ordinary skill may recognize alternatives to measuring the output signal and operational signal magnitudes. Such alternative measurements are expressly encompassed herein, whether now existing or later developed. Also, the prior patents incorporated herein by reference provide a discussion of the frequency offset used in prior ultrasonic imaging. In the various aspects of the calibration method herein, the output signal frequency preferably differs from the operational frequency by an amount sufficient to ensure discrimination, as can be appreciated from such incorporated patents. Preferably, the frequency offset is less than about ±10% of the operational frequency. As an example, for an operational frequency in the GHz range, the frequency offset can be in the kiloHertz (KHz) range. That is, the output signal frequency can equal the GHz operational frequency plus or minus a KHz value.

In keeping with the description of various imaging systems, such systems may further include a calibrations means for calibrating while producing an inspection signal. Preferably, the calibration means is compatible with producing a single-point, real-time signal. Any suitable optical and/or electronic components known to the those skilled in the art that may be used to perform the steps described for the calibration methods can constitute the calibration means. Specifically, an inspection system can include a calibration mechanism having at least an amplitude modulator that modulates a drive signal of a phase modulator, the phase modulator being of the type used to phase modulate a reference wavefront. The amplitude modulator thus produces two sideband signals of the modulated reference wavefront, the two sideband signals interfering in a photo-refractive material to provide a calibration output signal. The output signal may be used as indicated herein for calibration purposes.

According to another aspect of the invention, an inspection system calibration method includes phase modulating a reference wavefront, producing two sideband signals of the phase modulated reference wavefront, and interfering the two sideband signals in a photorefractive material, producing an output signal therefrom having a frequency and a magnitude. The method includes interfering the phase modulated reference wavefront with an object wavefront in a photorefractive material and producing an operational signal therefrom having a frequency different from the output signal frequency, a magnitude, and a phase modulation amplitude. The ratio of the operational signal magnitude to the output signal magnitude may be determined along with a ratio of a 1st order Bessel function of the operational signal phase modulation amplitude to a 0th order Bessel function of the operational signal phase modulation amplitude. The magnitude ratio may be compared to the Bessel function ratio.

Turning to FIG. 6, a chart is shown plotting both the magnitude ratio and the Bessel function ratio as a function of multiple values of the operational signal phase modulation amplitude. The plotted data may be easily compared in this form to check agreement of the magnitude ratio experimental values with the curve generated by the Bessel function ratio. If satisfactory agreement is not found, then investigation may be warranted regarding inspection system malfunction or compensation for various known effects that can be helpful in bringing the data into concurrence.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. An inspection system calibration method comprising:
    producing two sideband signals of a first wavefront;
    interfering the two sideband signals in a photorefractive material, producing an output signal therefrom having a frequency and a magnitude;
    producing a phase modulated operational signal having a frequency different from the output signal frequency, a magnitude, and a phase modulation amplitude; and
    determining a ratio of the operational signal magnitude to the output signal magnitude, determining a ratio of a 1st order Bessel function of the operational signal phase modulation amplitude to a 0th order Bessel function of the operational signal phase modulation amplitude, and comparing the magnitude ratio to the Bessel function ratio.

2. The method of claim 1 wherein producing two sideband signals comprises phase modulating the first wavefront with a phase modulator using an amplitude modulated drive signal.

3. The method of claim 1 wherein producing the phase modulated operational signal comprises phase modulating the first wavefront.

4. The method of claim 1 wherein producing the phase modulated operational signal comprises:
    phase modulating the first wavefront; and
    interfering the phase modulated first wavefront with an object wavefront in a photorefractive material.

5. The method of claim 4 further comprising phase modulating the object wavefront.

6. The method of claim 4 wherein the first wavefront comprises a reference wavefront, the object wavefront comprises a modulated object wavefront reflected from a vibrating subject surface, and the operational signal comprises a single-point, real-time signal of the subject surface, the method comprising acquiring the inspection signal simultaneously with determining the magnitude ratio.

7. The method of claim 1 wherein the output signal frequency differs from the operational signal frequency by at least about 10%.

8. The method of claim 1 wherein the output signal and operational signal magnitudes are measured as voltages and the magnitude ratio comprises a voltage ratio.

9. The method of claim 8 wherein the voltages comprise root-mean-square voltages.

10. The method of claim 1 wherein the two sideband signals and the operational signal are comprised by at least one laser beam.

11. The method of claim 1 further comprising plotting both the magnitude ratio and the Bessel function ratio as a function of multiple values of the operational signal phase modulation amplitude and comparing the plotted data.

12. The method of claim 1 wherein the inspection system comprises an optical microscope.

13. An inspection system calibration method comprising:
phase modulating a reference wavefront;
producing two sideband signals of the phase modulated reference wavefront;
interfering the two sideband signals in a photorefractive material, producing an output signal therefrom having a frequency and a magnitude;
interfering the phase modulated reference wavefront with an object wavefront in a photorefractive material and producing an operational signal therefrom having a frequency different from the output signal frequency, a magnitude, and a phase modulation amplitude; and
determining a ratio of the operational signal magnitude to the output signal magnitude, determining a ratio of a 1st order Bessel function of the operational signal phase modulation amplitude to a 0th order Bessel function of the operational signal phase modulation amplitude, and comparing the magnitude ratio to the Bessel function ratio.

14. The method of claim 13 wherein the phase modulating the reference wavefront occurs with a phase modulator and the producing two sideband signals comprises amplitude modulating a drive signal of the phase modulator.

15. The method of claim 13 wherein the output signal frequency differs from the operational signal frequency by at least about 10%.

16. The method of claim 13 wherein the output signal and operational signal magnitudes are measured as voltages and the magnitude ratio comprises a voltage ratio.

17. The method of claim 15 wherein the voltages comprise root-mean-square voltages.

18. The method of claim 13 wherein interfering the phase modulated reference wavefront with an object wavefront occurs in the same photorefractive material as interfering the two sideband signals.

19. The method of claim 13 wherein the reference and object wavefronts each comprise a laser beam.

20. The method of claim 13 further comprising plotting both the magnitude ratio and the Bessel function ratio as a function of multiple values of the operational signal phase modulation amplitude and comparing the plotted data.

21. The method of claim 13 comprising reflecting the object wavefront from a vibrating surface that modulates the object wavefront prior to interfering with the phase modulated reference wavefront.

22. The method of claim 13 wherein the inspection system comprises an optical microscope and the object wavefront passes though an objective of the microscope prior to interfering with the phase modulated reference wavefront.

23. The method of claim 22 wherein the object wavefront comprises a modulated object wavefront reflected from a vibrating surface of a subject of the microscope and the operational signal comprises a single-point, real-time signal of the subject surface, the method comprising acquiring the single-point signal simultaneously with determining the magnitude ratio.

24. An inspection system calibration method comprising:
phase modulating a reference beam with a phase modulator;
amplitude modulating a drive signal of the phase modulator and producing two sideband signals of the phase modulated reference beam;
interfering the two sideband signals in a photorefractive material, producing an output signal therefrom having a frequency and a magnitude, the magnitude being measured as a root-mean-square voltage;
passing an object beam though an objective of an optical microscope comprised by the inspection system and reflecting the object beam from a vibrating surface that phase modulates the object beam;
interfering the phase modulated reference beam with the phase modulated object beam in the photorefractive material, producing an operational signal therefrom having a frequency different from the output signal frequency, a magnitude measured as a root-mean-square voltage, and a phase modulation amplitude; and
determining a ratio of the operational signal voltage to the output signal voltage, determining a ratio of a 1st order Bessel function of the operational signal phase modulation amplitude to a 0th order Bessel function of the operational signal phase modulation amplitude, and comparing the voltage ratio to the Bessel function ratio.

25. An inspection method comprising:
providing an object wavefront that illuminates a vibrating surface of a subject and directing a modulated object wavefront returned from the vibrating surface to a photorefractive material;
phase modulating a reference wavefront;
producing two sideband signals of the modulated reference wavefront;
interfering the modulated reference wavefront with the modulated object wavefront in the photorefractive material, and producing an inspection signal of the vibrating surface having a frequency, a magnitude, and a phase modulation amplitude;
interfering the two sideband signals in the photorefractive material, producing an output signal therefrom having a frequency different from the inspection signal frequency and a magnitude; and
calibrating by determining a ratio of the inspection signal magnitude to the output signal magnitude, determining a ratio of a 1st order Bessel function of the inspection signal phase modulation amplitude to a 0th order Bessel function of the inspection signal phase modulation amplitude, and comparing the magnitude ratio to the Bessel function ratio.

26. The method of claim 25 further comprising acquiring the inspection signal, the acquiring occurring simultaneously with determining the magnitude ratio.

27. The method of claim 25 wherein the inspection signal comprises a single-point, real-time signal.

28. The method of claim 25 wherein the inspection signal comprises a full-field, real-time image signal.

29. The method of claim 28 further comprising additionally producing a simulated single-point, real-time signal simultaneously by blocking part of the image signal.

30. The method of claim 25 further comprising passing the object wavefront though an objective of an optical microscope and returning the modulated object wavefront through the objective prior to interfering with the phase modulated reference wavefront.

31. The method of claim 25 wherein the reference and object wavefronts each comprise a laser beam.

* * * * *